(12) United States Patent
Stadeker

(10) Patent No.: US 7,766,655 B2
(45) Date of Patent: Aug. 3, 2010

(54) SELF-CONTAINED DENTAL PROPHYLAXIS ANGLE WITH OFFSET ROTATIONAL AXIS

(75) Inventor: Wilkie J. Stadeker, Marietta, GA (US)

(73) Assignee: Medipurpose PTE Ltd, Norcross, GA (US)

( * ) Notice: Subject to any disclaimer, the term of this patent is extended or adjusted under 35 U.S.C. 154(b) by 57 days.

(21) Appl. No.: 11/421,081

(22) Filed: May 31, 2006

(65) Prior Publication Data

US 2006/0204923 A1   Sep. 14, 2006

Related U.S. Application Data

(63) Continuation-in-part of application No. 10/909,816, filed on Aug. 2, 2004, now Pat. No. 7,070,412.

(51) Int. Cl.
*A61C 1/10* (2006.01)
*A61C 3/06* (2006.01)

(52) U.S. Cl. .................................. 433/82; 433/125

(58) Field of Classification Search ............ 433/83, 433/125, 166, 82, 85, 87
See application file for complete search history.

(56) References Cited

U.S. PATENT DOCUMENTS

| | | | |
|---|---|---|---|
| 2,400,912 A | 5/1946 | Britt | |
| 2,738,528 A | 3/1956 | Fridge | |
| 3,195,537 A * | 7/1965 | Blasi | 601/114 |
| 3,389,468 A | 6/1968 | Lewis | |
| 3,579,835 A | 5/1971 | Levenson | |
| 4,097,995 A | 7/1978 | Danne | |
| 4,173,828 A * | 11/1979 | Lustig et al. | 433/87 |
| 5,209,658 A | 5/1993 | Brahler | |
| 5,234,688 A | 8/1993 | Gaffar | |
| 5,340,310 A | 8/1994 | Bifulk | |
| 5,352,119 A | 10/1994 | Sakurai | |
| 5,380,202 A | 1/1995 | Brahler | |
| 5,482,461 A | 1/1996 | Yale | |
| 5,531,599 A | 7/1996 | Bailey | |
| 5,571,012 A | 11/1996 | Witherby et al. | |
| 5,642,994 A | 7/1997 | Chipian | |
| 5,642,995 A | 7/1997 | Bailey | |
| 5,645,426 A | 7/1997 | Grim et al. | |
| 5,667,383 A | 9/1997 | Mendoza et al. | |
| 5,690,488 A | 11/1997 | Spinello | |
| 5,692,901 A | 12/1997 | Roth et al. | |
| 5,730,595 A | 3/1998 | Bailey | |

(Continued)

*Primary Examiner*—Cris L Rodriguez
*Assistant Examiner*—Yogesh Patel
(74) *Attorney, Agent, or Firm*—Ryan A. Schneider, Esq.; Seyed Kaveh E. Rashidi-Yazd, Esq.; Troutman Sanders LLP

(57) ABSTRACT

The present invention discloses a self-contained dental prophylaxis angle with a separate therapeutic content lumen and drive shaft lumen. The phrophylaxis angle also provides an offset rotational axis and methods for its use in cleaning, polishing, bleaching, bonding, etching, abrading, desensitizing, or otherwise treating teeth. An offset drive system is provided to power rotation of the dental tip in a system that can be physically separated from the storage and dispensing system for therapeutic content. A self-contained dental prophylaxis angle with an offset rotational axis according to the present invention may be used with a variety of shaped dental tips of varying degrees of rigidity, according the needs of a given clinical application.

2 Claims, 7 Drawing Sheets

U.S. PATENT DOCUMENTS

| | | |
|---|---|---|
| 5,743,718 A | 4/1998 | Mendoza et al. |
| 5,871,353 A | 2/1999 | Pierce et al. |
| 5,911,577 A | 6/1999 | Henrikson |
| 5,984,654 A | 11/1999 | Mendoza et al. |
| 6,053,732 A | 4/2000 | Sale |
| 6,164,967 A | 12/2000 | Sale |
| 6,206,600 B1 | 3/2001 | Rosenberg |
| 6,257,886 B1 | 7/2001 | Warner |
| 6,382,971 B1 | 5/2002 | Randolph |
| 6,632,090 B1 | 10/2003 | Randolph |
| 6,875,017 B1 | 4/2005 | Tarr |
| 6,902,337 B1 * | 6/2005 | Kuo ....................... 401/188 R |
| 7,101,182 B2 | 9/2006 | Garrison |
| 2004/0106083 A1 * | 6/2004 | Pond ......................... 433/125 |
| 2005/0042571 A1 | 2/2005 | Calvert |
| 2007/0111159 A1 | 5/2007 | Stadeker |

* cited by examiner

SELF-CONTAINED DENTAL PROPHYLAXIS ANGLE WITH OFFSET ROTATIONAL AXIS

CROSS-REFERENCE TO RELATED APPLICATIONS

This application is a continuation-in-part application of copending U.S. patent application Ser. No. 10/909,816, filed on Aug. 2, 2004, allowed, which is hereby incorporated in its entirety.

FIELD OF THE INVENTION

The present invention relates generally to the field of dental devices, and relates more specifically to a self-contained dental prophylaxis angle with an offset rotational axis and methods for use in cleaning, polishing, bleaching, bonding, etching, abrading, desensitizing, or otherwise treating teeth.

BACKGROUND OF THE INVENTION

The application of an abrasive dentifrice paste is generally known to clean and polish teeth. Similarly, other dentifrice compounds are applied to the surfaces of teeth in numerous other dental procedures to bleach, abrade, or otherwise treat a variety of dental conditions. Most commonly, such procedures are performed by a dentist, dental hygienist, or dental assistant using a motorized handpiece which receives what is commonly referred to in the art as a "prophylaxis angle" or "prophy angle." Typically, the prophylaxis angle is mounted at a right angle to the handpiece, and has a rotating polishing surface that is rotated by the motorized action of the handpiece, and receives dentifrice as it rotates from a cup mounted on the prophylaxis angle. The dentifrice contained within the cup on the prophylaxis angle is replaced as needed by the operator, typically by dipping the prophylaxis angle into a container of dentifrice and scooping out additional dentifrice as desired.

As conventionally deployed, the dentifrice used in prophylaxis angles has been generally in a paste, cream, or other gummy amalgam form. Powdered dentifrices have also been commonly used, generally with sufficient moisture added to create a paste-like preparation for application.

Formerly, most prophylaxis angles were supplied and used as multi-use devices, requiring cleaning and/or sterilization between use for different patients. With the advent of cost-efficient, disposable manufacturing materials and techniques, and with the growing concern over the prevention of transmittable diseases during dental therapy, the use of single-use, disposable prophylaxis angles has become commonplace.

Although the development of disposable prophylaxis angles has had significant impact on dental practice, problems still exist relating to the application of dentifrice to a patient's teeth using an existing disposable prophylaxis angle. Conventional disposable prophylaxis angles may effectively prevent the spread of disease from patient to patient, but do not completely protect the dentist or other operator from potential exposure during use. The container of dentifrice is often held on the finger of the operator. Digital pressure must then be employed with the dentifrice to apply it to the cup of the prophylaxis angle, and such pressure may often stall the drive motor that drives the prophylaxis angle. As the digital pressure is released, the drive motor overcomes the stalling pressure, and the rotational speed of the prophylaxis cup may suddenly increase, potentially spraying buccal debris such as saliva, blood, and tissue particles into the surrounding work environment. This phenomenon is commonly referred to as "splatter," and may occur even in the presence of a minimal amount of buccal debris. Exposure to such debris can pose a significant health risk to the dentist and/or other operators who are attending the patient.

Past attempts have been made to incorporate dispensable dentifrice within the prophylaxis angle device. However, these efforts have generally failed because of technical disadvantages that prevented their acceptance in the dental marketplace. Among other problems, early prophylaxis angles incorporating paste were not disposable. Additionally, other paste delivery mechanisms were relatively mechanically complex and therefore cost prohibitive.

For example, disposable prophylaxis angles having internal paste delivery systems using an auger-like structure of the type proposed in the related art must overcome problems associated with charging an internal reservoir with dentifrice material either before or after the auger is assembled into the prophylaxis angle. Either way, the helical blades of the auger, which typically extend for a substantial portion of the internal diameter of the fluid reservoir, make it difficult to fully charge the reservoir with the dentifrice material. Also, the auger blades make advancement of the dentifrice material dependent on the direction of rotation and rotational speed of the auger.

Prophylaxis angles as previously known in the related art are also too large to be practical or were generally more difficult to use and required retraining the practitioner before use on a patient.

Recent efforts to improve a prophylaxis angle are disclosed in U.S. Pat. No. 6,257,886 to Warner, U.S. Pat. No. 6,382,971 to Randolph, U.S. Pat. No. 5,692,901 to Roth et al., and U.S. Pat. No. 5,871,353 to Pierce et al. These cited prophylaxis angles, while they may represent improvements upon certain aspects of the preceding art, continue to be designed around a central rotational axis, which requires more complex engineering to allow for a pathway for dentifrice flow. Certain deficiencies also persist among existing prophylaxis angles, leaving a need for further improvement in the design, use, and applications for such devices.

SUMMARY OF THE INVENTION

A prophylaxis angle according to the present invention overcomes, or at least alleviates, one or more of the difficulties or deficiencies associated with prior art prophylaxis angles, employing an offset rotational axis which allows mechanically simpler and more reliable passage of dentifrice material during use.

A prophylaxis angle according to the present invention may or may not require a cup to receive dentifrice or other dental therapeutic material as is commonly employed in existing prophylaxis angles in cleaning or otherwise treating teeth. In a prophylaxis angle according to the present invention in which a modified cup is employed, a supply of dentifrice or other dental therapeutic material is delivered in the proximity of or through the cup through one or more channels parallel to the rotational axis of the power drive, which is offset from a central axis within the handle of the prophylaxis angle. In a prophylaxis angle according to the present invention in which no cup is required, a dentifrice or other dental therapeutic material is dispensed within the prophylaxis angle, and the dentifrice or other dental therapeutic material is dispensed in the proximity of or through the surface tip that cleans or otherwise contacts the teeth for the desired effect.

A prophylaxis angle according to the present invention may further incorporate a control device to start or stop rotational action of the prophylaxis angle for enhanced user control and convenience. Moreover, a prophylaxis angle according to the present invention may further incorporate an adjustable geared mechanism to allow user control of the rotational speed of the prophylaxis angle.

A prophylaxis angle according to the present invention may further provide a design that will not allow back flow of saliva or contaminated materials into the unused dentifrice supply.

A prophylaxis angle according to the present invention may be provided either as a single use, disposable device, or as a reusable device for various applications.

A prophylaxis angle according to the present invention may be provided for a variety of therapeutic applications in the fields of dentistry and oral hygiene. Such applications include, but are not limited to, the cleaning, polishing, etching, desensitization, bonding, abrading, fluoride treatment of teeth, gums, other intraoral structures, dental appliances, or other dental therapeutic or oral hygienic procedures.

A prophylaxis angle according to the present invention may be provided to mechanically interface with the nozzle connector piece of a standard dental gas-driven handpiece to provide power for use in dental therapeutic or oral hygienic procedures.

In alternate embodiments according to the present invention, a prophylaxis angle according to the present invention may be provided to incorporate a connection allowing direct connection to the motor unit of a standard dental gas-driven handpiece to provide power for use in dental therapeutic or oral hygienic procedures, thus eliminating the need to clean and re-sterilize conventional nozzle connectors for such headpieces.

A prophylaxis angle according to the present invention may be provided as a toothbrush for self use by patients.

A method of treating teeth using a self-contained dental prophylaxis angle according to the present invention by an operator or by a patient, in which a dental therapeutic material contained within the dental prophylaxis is delivered to the interface of a powered dental tip and the teeth while power is applied to rotate the dental tip through a drive mechanism which is offset from the mechanical center of the dental prophylaxis unit.

These and other features, aspects, and other advantages of the present invention will become better understood with regard to the following drawings, description, and appended claims.

DETAILED DESCRIPTION OF THE INVENTION

Figure 1:
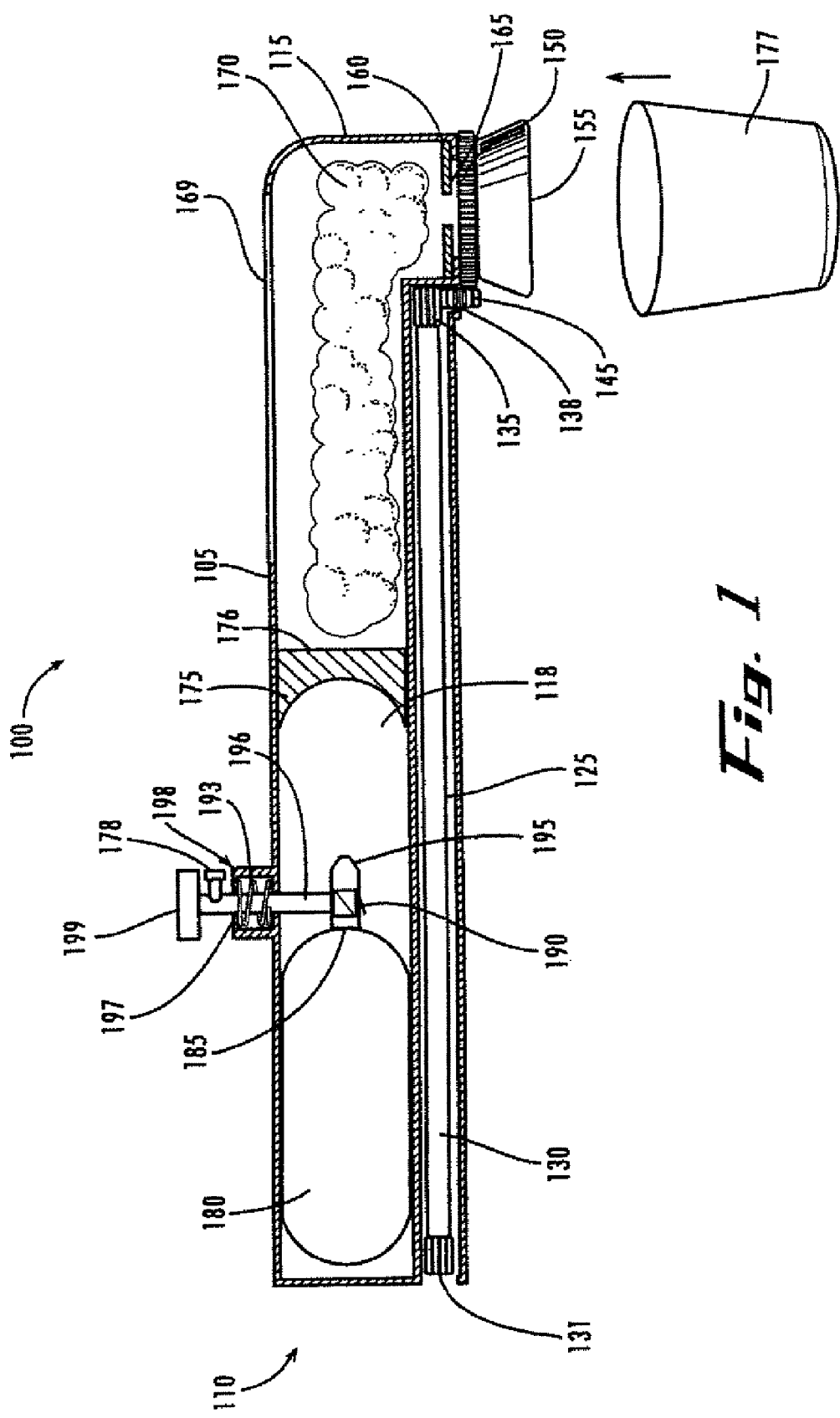
FIG. 1 provides a cross-sectional view of an exemplary self-contained dental prophylaxis angle with an offset rotational axis according to the present invention in which a contained pressurized gas is used to advance the flow of dentifrice within.

The present invention may be understood more readily by reference to the following detailed description of the preferred embodiments of the invention and the Examples included herein. However, before the preferred embodiments of the devices and methods according to the present invention are disclosed and described, it is to be understood that this invention is not limited to the exemplary embodiments described within this disclosure, and the numerous modifications and variations therein that will be apparent to those skilled in the art remain within the scope of the invention disclosed herein. It is also to be understood that the terminology used herein is for the purpose of describing specific embodiments only and is not intended to be limiting.

Unless otherwise noted, the terms used herein are to be understood according to conventional usage by those of ordinary skill in the relevant art. In addition to the definitions of terms provided below, it is to be understood that as used in the specification and in the claims, "a" or "an" can mean one or more, depending upon the context in which it is used.

The present invention is directed towards a self-contained dental prophylaxis angle with an offset rotational axis and methods for its use in performing dental therapeutic procedures. Such dental therapeutic procedures, as referred to herein, include, but are not limited to, the cleaning, polishing, etching, desensitization, bonding, abrading, fluoride treatment of teeth, gums, other intraoral structures, dental appliances, or other dental therapeutic or oral hygienic procedures.

In an exemplary embodiment according to the present invention, a self-contained dental prophylaxis angle with an offset rotational axis is provided to dispense dentifrice or other therapeutic medicament contained therein as the prophylaxis angle is being used by an operator to clean or otherwise treat a patient's teeth. An exemplary self-contained dental prophylaxis angle with an offset rotational axis according to the present invention is provided with an elongated tubular body with a length defining a central axis, a proximal end, a distal end, a content lumen containing a content in fluid communication with a distal content portal, and a drive lumen in communication with a distal drive portal. In addition, such a self-contained dental prophylaxis angle with an offset rotational axis according to the present invention is farther provided with a dental tip rotatably mounted on the distal end that is turned by the action of one or more distal gears at the distal drive portal that are turned by a mechanical drive shaft within the drive lumen and with a length defining a longitudinal rotational axis. Finally, a self-contained dental prophylaxis angle with an offset rotational axis according to the present invention is provided with a content dispensing mechanism to selectively dispense content such as a dental therapeutic dentifrice or other material from the content lumen through the distal content portal into contact or proximity with the dental tip.

Referring now to the drawings, in which like numerals indicate like elements throughout the several views, one preferred embodiment of an exemplary prophylaxis angle according to the present invention is shown in FIG. 1. As shown in FIG. 1, an exemplary self-contained dental prophylaxis angle 100 is provided with a tubular body 105 with a proximal end 110 and a distal end 115. In various embodiments according to the present invention, the external shape of the body 105 may be round, oblong, triangular, square, polygonal, or any other desired shape. In the example illustrated in FIG. 1, the body 105 contains at least two parallel lumens, a main lumen 118, and a drive lumen 125. The longitudinal axis of the main lumen 118 is referred to herein as the central axis. The drive lumen contains a drive shaft 130. The longitudinal axis of the drive shaft 130 is referred to herein as the rotational axis. At the proximal end 110, the drive shaft 130 is fitted with a geared connector 131 compatible to connect operably with a standard dental handpiece [not shown] to provide rotational power to said drive shaft 130. The drive shaft 130 is further provided with a distal gear tip 135 which interfaces with a transitional gear 145 which interfaces with a geared tip 150 at a distal drive portal 138 to transfer rotational motion from the handpiece to the geared tip 150 thus rotating a cleaning tip 155 which is attached to said geared tip 150.

In alternate embodiments according to the present invention, the distal gear tip 135 may interface directly with the geared tip 150 at a distal drive portal 138, eliminating any transitional gears. The cleaning tip 155 and attached geared tip 150 are rotatably attached to the distal end 115 of the body 105, which may be straight, or may be curved at an angle varying from 0 to 179 degrees with respect to the long axis of the body 105. At or near the junction with the dental tip 155 and attached geared tip 150, the body 105 terminates with a content portal 160 which contains one or more fenestrations 165 to allow egress of therapeutic content 170 from main lumen 118 onto or in proximity with the dental tip 155 for cleaning or other therapeutic purposes. Flow of said egress of contained dentifrice or other therapeutic content 170 from main lumen 118 is effected by compression by a plunger 175 with a distal face 176. In various embodiments according to the present invention, the plunger 175 is sized and shaped to fit sealably, but slidably within the main lumen 118. The distal face 176 of the plunger 175 may be flat, concave, convex, or otherwise shaped to fit the desired application. In the example shown in FIG. 1, the plunger 175 is advanced by the effect of gas pressure release from a pressurized gas container 180 located within the proximal aspect of main lumen 118. Said pressurized gas container 180 has a gas portal 185 that connects to a gas valve 190 and a gas jet 195. The gas valve 195 is operated by compression action of a control stem 196 which is spring loaded by a spring 193 which is housed in a control well 198. The control stem 196 has a sealed traverse through said control well 198, and exits through a sealed control well cap 197 to terminate in a control button 199.

In various embodiments according to the present invention, the control button 199 may be provided further with a control latch 178 to permit continued opening of the gas valve 190 despite release of digital pressure by the operator. Such a control latch 178 would be immediately releasable upon a re-application of digital pressure to the control button 199 by the operator.

In use by an operator, the exemplary prophylaxis angle of FIG. 1 is again attached to a standard dental handpiece. The rotary motion of the handpiece powers the motion of the drive shaft 130, which is transferred to, and causes rotational motion of the dental tip 155. When the operator desires to effect the dispensing of therapeutic content 170, digital pressure on the control button 199 opens the gas valve 190, releasing compressed gas into the enclosed main lumen 118, thus permitting the displacement of the plunger 175 and dispensing therapeutic content 170 through the fenestrations 165 in the end cap 160. In various embodiments according to the present invention, the body 105 may further be provided with one or more transparent windows 169 that permit an operator to monitor the movement of the plunger 175 towards the distal end 115, thus allowing the operator to determine how much content 170 remains to be dispensed. Graduations or other markers [not shown] may be provided on the windows 169 to allow the operator to quantitate the remaining content 170.

In other alternate embodiments according to the present invention, a self-contained dental prophylaxis angle 100 may further be provided with a distal cap 177 removable by the operator, which may serve to provide a seal during storage, and to prevent inadvertent leakage of content 170 prior to use.

In yet other alternate embodiments according to the present invention, the distal end 115 may be covered by a membrane [not shown]. Such a membrane may be solid and removable or pierced by the operator prior to use, or may be semipermeable, and permit egress of content 170 through the membrane as the plunger 175 is advanced.

In yet other alternate embodiments according to the present invention, content is dispensed by action of a plunger which is advanced by the effect of gas pressure release from a pressurized gas located within the main lumen operable by a valve activated by a user in a manner similar to a conventional aerosol can. Alternately, content may be dispensed by direct action of a pressurized gas located within the main lumen operable by a valve activated by a user in a manner similar to a conventional aerosol can. Alternately still, a self-contained dental prophylaxis angle according to the present invention may be directly connected to an external source of compressed gas, such as that typically provided in a dental treatment unit, to dispense content either by advancing a plunger or by direct displacement effect on the content.

Figure 2:
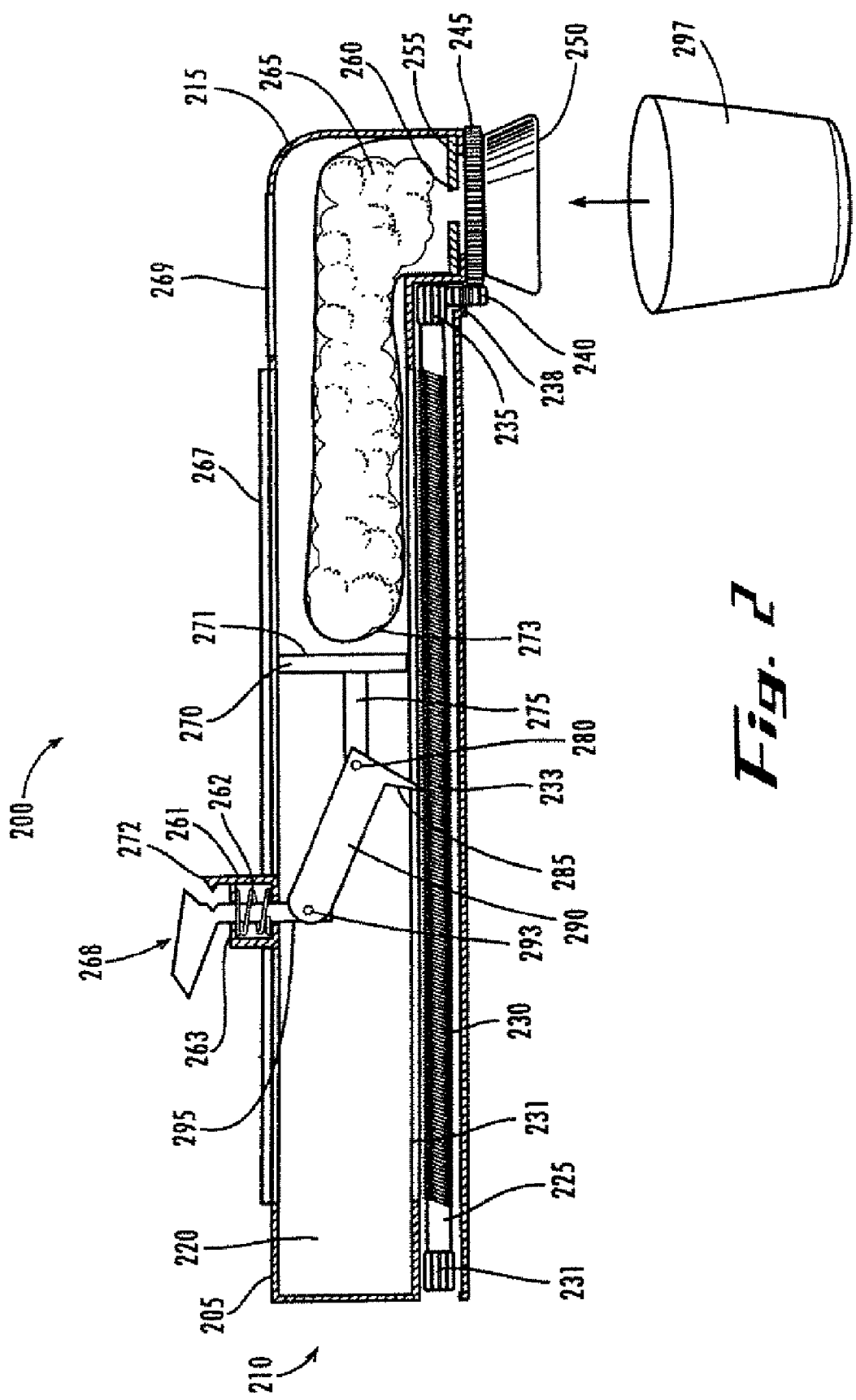
FIG. 2 provides a cross-sectional view of an exemplary self-contained dental prophylaxis angle with an offset rotational axis according to the present invention in which the mechanical action of the prophylaxis angle is used to advance the flow of dentifrice within.

An alternate preferred embodiment of an exemplary prophylaxis angle according to the present invention is shown in FIG. 2. As shown in FIG. 2, an exemplary self-contained dental prophylaxis angle 200 is provided with an elongated tubular body 205 with a proximal end 210 and a distal end 215. In various embodiments according to the present invention, the external shape of the body 205 may be round, oblong, triangular, square, polygonal, or any other desired shape. In the example illustrated in FIG. 2, the body 205 contains at least two parallel lumens, a main lumen 220, and a drive lumen 225. The longitudinal axis of the main lumen 220 is referred to herein as the central axis. The drive lumen contains a turnable drive shaft 230 which contains drive shaft threads 233 along some or all its length. The longitudinal axis of the drive shaft 230 is referred to herein as the rotational axis. At the proximal end 210, the drive shaft 230 is fitted with a geared connector 231 compatible to connect operably with a standard dental handpiece [not shown] to provide rotational power to said drive shaft 230. The drive shaft 230 is further provided with a distal gear tip 235 which interfaces at a distal drive portal 238 with a transitional gear 240 which interfaces with a geared tip 245 to transfer rotational motion from the handpiece to the geared tip 245 thus rotating a cleaning tip 250 which is attached to said geared tip 245. In alternate embodiments according to the present invention, the distal gear tip 235 may interface directly with the geared tip 245 at a distal drive portal 238, eliminating any transitional gears. The cleaning tip 250 and attached geared tip 245 are rotatably attached to the distal end 215 of the body 205, which may be straight, or may be curved at an angle varying from 0 to 179 degrees with respect to the long axis of the body 205. At the junction with the dental tip 250 and attached geared tip 245, the body 205 terminates with a content portal 255 which contains one or more fenestrations 260 to allow egress of therapeutic content 265 from main lumen 220 onto or in proximity with the dental tip 250 for cleaning or other therapeutic purposes. In various embodiments according to the present invention, the therapeutic content 265 may be contained within the main lumen 220 within a content sac 273 which may be attached to the content portal 255 such that content can only be expressed through the content portal 255 upon compression of the sac 273 and leakage of content 265 is otherwise avoided. Such a content sac 273 may be fabricated of any thin, flexible, and compressible material such as a plastic, rubber, or other natural or synthetic polymer that is chemically inert with respect to the nature of the therapeutic content 265. Flow of said egress of contained dentifrice or other therapeutic content 265 from lumen 220 is effected by compression by a plunger 270 with a distal face 271. In various embodiments according to the present invention, the plunger 270 is sized and shaped to fit sealably, but slidably within the main lumen 220. The distal face 271 of the plunger 270 may be flat, concave, convex, or otherwise shaped to fit the desired application. In the example shown in FIG. 2, the plunger 270 is attached to a stem 275 to which an engagement arm 290 is attached at a first engagement pivot 280. The engagement arm 290 is further provided with an engagement pin 285. The engagement pin 285 is provided to engage the drive shaft threads 233 through an engagement slot 231 that connects lumens 220 and 225 within body 205. The engagement arm 290 is further attached at a second engagement pivot 293 to a control stem 295. The control stem 295 passes from main lumen 220 through the wall of the body 205 in a control well 261. Within said control well 261, a spring 262 between the body 20 and a control well cap 263 maintains tension on said control stem 295 and engagement arm 290. For user convenience, the control stem 295 may be attached to a control button 268. The control well 261 and its contained elements are slidably mounted in an advancement slot 267 that extends through said body 205 to allow advancement of said plunger 270 to dispense said therapeutic content 265.

In use by an operator, the exemplary prophylaxis angle of FIG. 2 is attached to a standard dental handpiece. The rotary motion of the handpiece powers the motion of the drive shaft 230, which is transferred to, and causes rotational motion of the dental tip 250. Also, the engagement of the engagement pin 285 by the drive shaft threads 233 allows the rotation of the drive shaft to effect movement of the plunger 270, along with the attached engagement arm/control stem assembly as described above which slides within the advancement slot 267. Should the operator desire to slow the dispensing of therapeutic content 265, digital pressure on the control button 268 causes the engagement pin 285 to disengage from the drive shaft threads 233, thus interrupting further displacement of the plunger 270 by handpiece rotational motion. When the operator desires to resume dispensing of therapeutic content 265, release of digital pressure on the control button 268 causes the engagement pin 285 to re-engage the drive shaft threads 233, thus permitting the renewed displacement of the plunger 270 by handpiece rotational motion. In various embodiments according to the present invention, the control button 268 may be provided further with a control latch 272 to permit continued engagement of the engagement pin 285 with the drive shaft threads 233 despite release of digital pressure by the operator. Such a control latch 272 would be immediately releasable upon a re-application of digital pressure to the control button 268 by the operator.

In various embodiments according to the present invention, the body 205 may further be provided with one or more transparent windows 269 that permit an operator to monitor the movement of the plunger 270 towards the distal end 215, thus allowing the operator to determine how much content 265 remains to be dispensed. Graduations or other markers [not shown] may be provided on the windows 269 to allow the operator to quantitate the remaining content 265.

In other alternate embodiments according to the present invention, a self-contained dental prophylaxis angle 200 may further be provided with a distal cap 297 removable by the operator, which may serve to provide a seal during storage, and to prevent inadvertent leakage of content 265 prior to use.

In yet other alternate embodiments according to the present invention, the distal end 215 may be covered by a membrane [not shown]. Such a membrane may be solid and removable or pierced by the operator prior to use, or may be semipermeable, and permit egress of content 265 through the membrane as the plunger 270 is advanced.

While the embodiment as described above has a separate main lumen 220 and drive lumen 225, in alternate embodiments according to the present invention, a common single lumen accommodates both the drive shaft and content storage/delivery functions.

Figure 3:
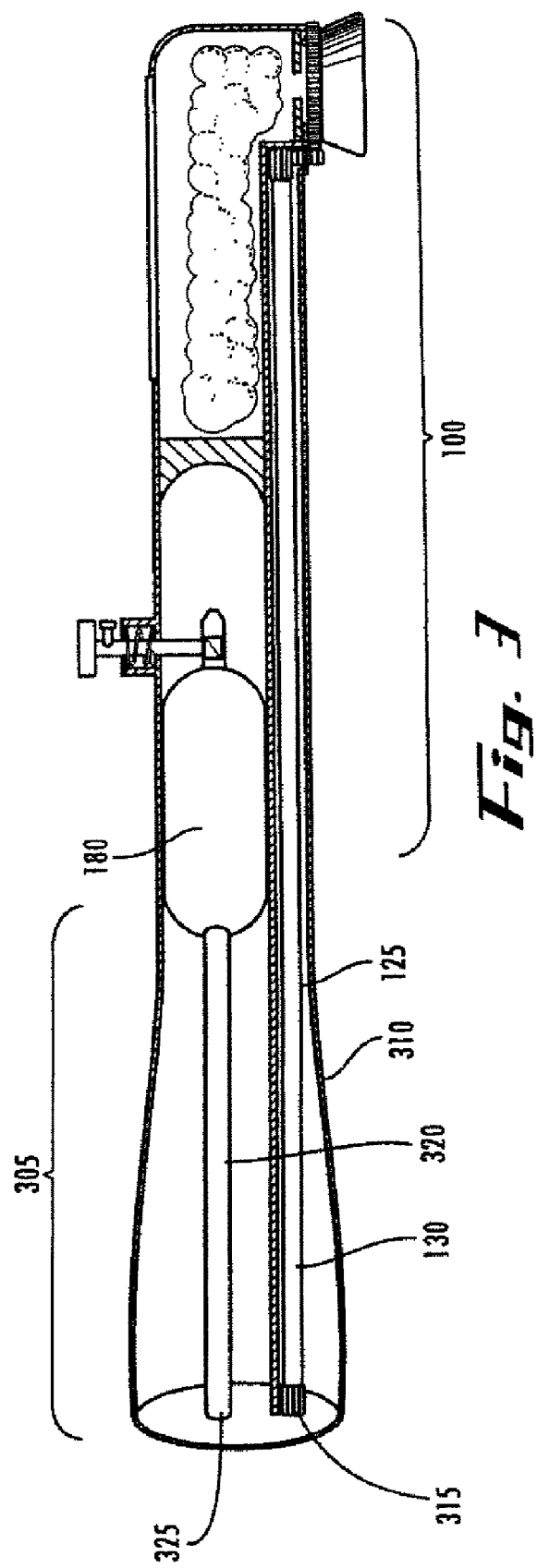
FIG. 3 provides a cross-sectional view of an exemplary self-contained dental prophylaxis angle with an offset rotational axis according to the present invention in which an integral nozzle is provided to directly connect to a standard dental handpiece motor unit.

In an alternate embodiment according to the present invention as shown in FIG. 3, a self-contained dental prophylaxis unit 100 similar to the one described above and in FIG. 1 is further provided with an attached or integrated nozzle segment 305, including a tubular nozzle body 310 which may be straight or flared, and contains an extension of the drive shaft 130 and drive lumen 125, with a drive gear 315 which directly interfaces with the motor gear of a standard dental handpiece motor [not shown]. Such alternate embodiments according to the present invention in which a nozzle segment 305 is provided as an attached or integral attachment to a self-contained dental prophylaxis unit 100 may include a self contained compressed gas tank, as shown previously above and in FIG. 1, to provide a mechanism to drive the dispensing of content. Alternately, when a self-contained dental prophylaxis unit 100 is provided with a nozzle segment 305 as shown in FIG. 3, a nozzle gas connector 320 may be provided with a tank connector 325 in gas flow continuity with the compressed gas tank 180, and with a handpiece gas connector 335 sized and located to connect with the compressed gas connectors on a standard dental compressed gas handpiece motor [not shown].

Figure 4:
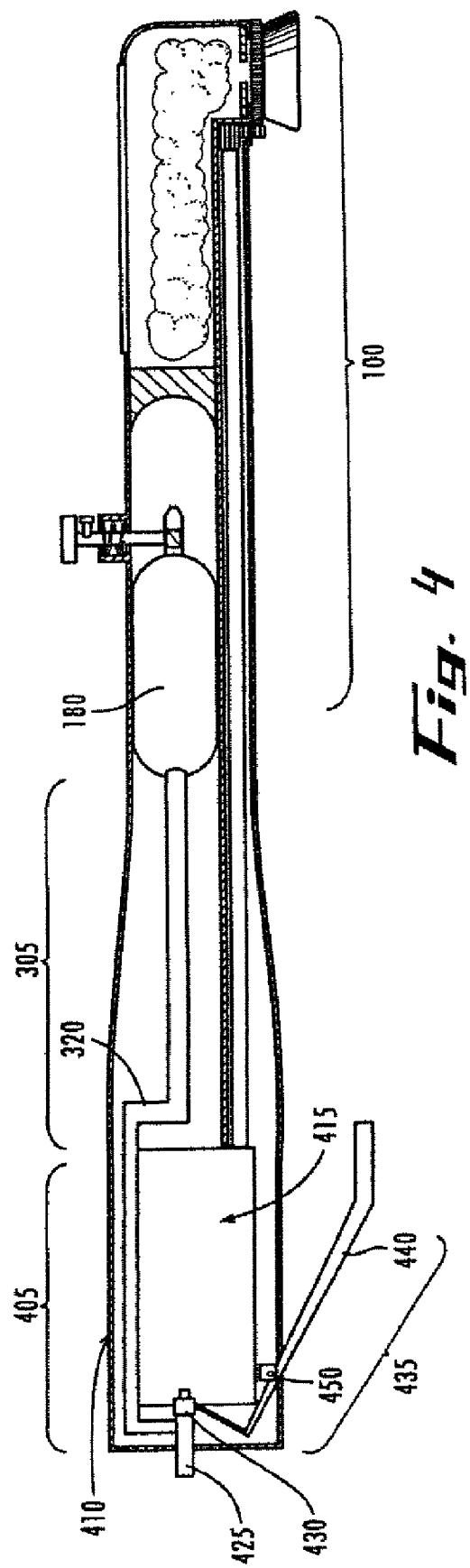
FIG. 4 provides a cross-sectional view of an exemplary self-contained dental prophylaxis angle with an offset rotational axis according to the present invention in which an integral nozzle and gas-driven motor unit is provided for direct connection to a standard dental compressed drive gas supply.

Yet another alternate embodiment according to the present invention is shown in FIG. 4. In this example, a self-contained dental prophylaxis unit 100 similar to the one described above and in FIG. 1 is provided with an attached or integrated nozzle segment 305 as described above and in FIG. 3, with the further attachment or integration of a motor segment 405 including a tubular or solid motor housing 410, a commonly available compressed gas-driven motor 415 of conventional design for use in standard dental handpieces, and one or more gas supply connectors 425 sized and located to permit attachment of the entire motor segment 405, nozzle segment 305, and prophylaxis angle 100 to a conventional dental handpiece supply line [not shown]. Various embodiments according to the present invention may employ branching compress gas supply lines to drive both the motor 415 and to supply compressed gas to the nozzle gas connector 320 to supply a compressed gas tank 180 when an external supply is used to drive the content dispensing function. When a dental prophylaxis angle is provided with an integral or attached motor unit 415 according to the present invention, a motor speed control valve 430 may further be provided with an attached motor speed control device 435 which may be a lever 440 pivotably mounted 445 to a pivot mount 450, such that pressure on the lever 440 may open the flow of compressed gas through the control valve 430, allowing the motor 415 to turn with increased speed. The action of this lever 440 may be spring-loaded or otherwise controlled mechanically [not shown], such that release of pressure on the lever 440 by an operator causes the motor 415 to slow or stop. Alternately, other mechanical, electrical, or electromechanical speed control connections may be provided between the control lever 445 or alternate control interface and the control valve 430, providing other conventional mechanisms to decrease or increase motor speed by adjusting the flow of compressed gas to the motor 415. The action of the speed control device 435 thus allows an operator to regulate the flow of compressed gas to the motor 415 to control its operation and operating speed.

Figure 5:
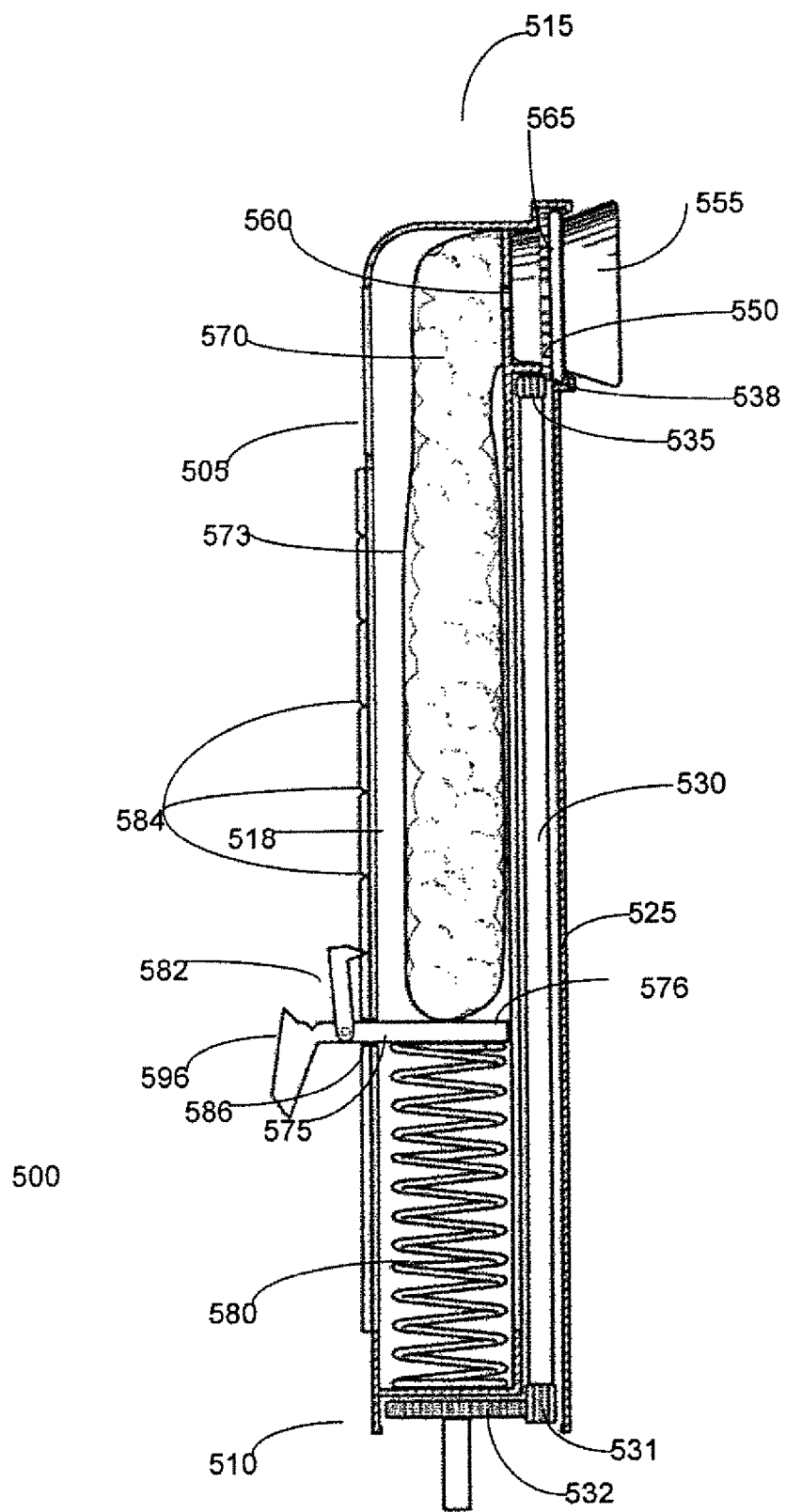
FIG. 5 provides a cross-sectional view of an exemplary self-contained dental prophylaxis angle with an offset rotational axis according to the present invention in which a spring biases the plunger distally.

Yet another alternate embodiment according to the present invention is shown in FIG. 5. As shown in FIG. 5, an exemplary self-contained dental prophylaxis angle 500 is provided with a tubular body 505 with a proximal end 510 and a distal end 515. In various embodiments according to the present invention, the external shape of the body 505 may be round, oblong, triangular, square, polygonal, or any other desired shape. In the example illustrated in FIG. 5, the body 505 contains at least two parallel lumens, a main content lumen 518, and a separate drive lumen 525. The longitudinal axis of the main lumen 518 is referred to herein as the central axis. The drive lumen contains a drive shaft 530. The longitudinal axis of the drive shaft 530 is referred to herein as the rotational axis. At the proximal end 510, the drive shaft 530 extends along at least the proximal end 510 of the body 505 and is fitted with a geared connector 531 which interfaces with a transitional gear 532 compatible to connect operably with a standard concentric drive dental handpiece [not shown] to provide rotational power to said drive shaft 530. The drive shaft 530 is further provided with a distal gear tip 535 which interfaces with a geared tip 550 at a distal drive portal 538 to transfer rotational motion from the handpiece to the geared tip 550 thus rotating a cleaning tip 555 which is attached to said geared tip 550.

In alternate embodiments according to the present invention, the cleaning tip 555 and attached geared tip 550 are rotatably attached to the distal end 515 of the body 505, which may be straight, or may be curved at an angle varying from 0 to 179 degrees with respect to the long axis of the body 505. At or near the junction with the dental tip 555 and attached geared tip 550, the body 505 terminates with a content portal 560 which contains one or more fenestrations 565 to allow egress of therapeutic content 570 from main lumen 518 onto or in proximity with the dental tip 555 for cleaning or other therapeutic purposes. Flow of said egress of contained dentifrice or other therapeutic content 570 from main lumen 518 is effected by compression by a plunger 575 with a distal face 576. In various embodiments according to the present invention, the plunger 575 is sized and shaped to fit sealably, but slidably within the main lumen 518. The distal face 576 of the plunger 575 may be flat, concave, convex, or otherwise shaped to fit the desired application. The therapeutic content 570 is shown contained within a content sac 573 in the main lumen 518.

In the example shown in FIG. 5, the plunger 575 is advanced by the effect of a spring 580 within the proximal aspect of main lumen 518 loading pressure upon the plunger 575. The plunger 575 is operated by compression action of a control stem 596 which disengages engagement pin 582 from anchoring to dispensing notches 584 on the tubular body 505 to provide pressure upon the therapeutic content 570 to exit the content portal 560. The control stem 596 advances toward the distal end 515 of the content containing main lumen 518 along an advancement slot 586, assisted by spring 580 pressure against the plunger 576. The engagement pin 582 is immediately renegagable with successive dispensing notches 584 upon a release of digital pressure from the control stem 596 by the operator. The control stem 596 is optionally also spring loaded (not shown) to maximize re-engagement and cessation of pressure on the therapeutic content 565.

Figure 6:
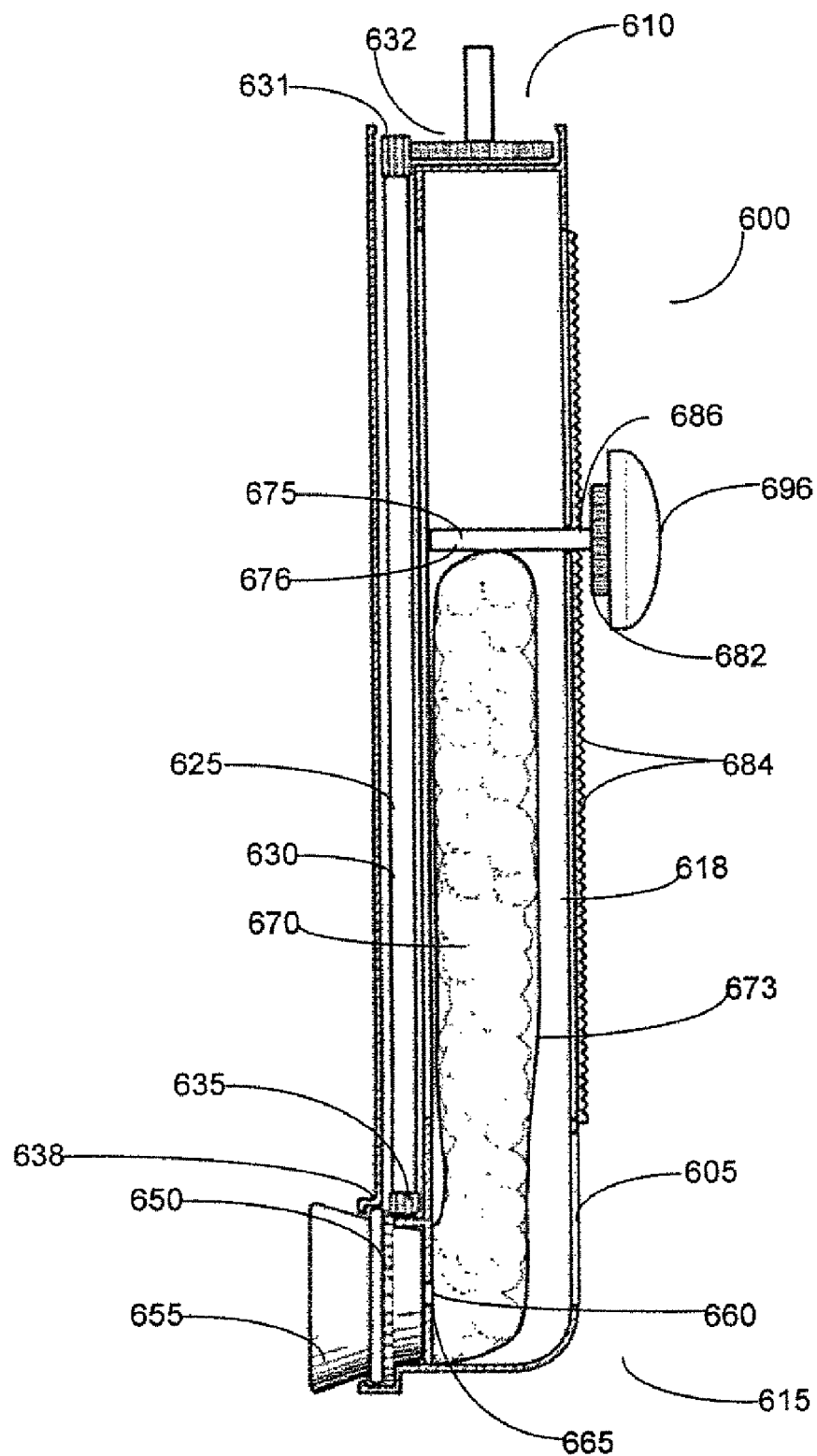
FIG. 6 provides a cross-sectional view of an exemplary self-contained dental prophylaxis angle with an offset rotational axis according to the present invention in which a threaded control stem actuates the plunger distally.
Figure 7A:
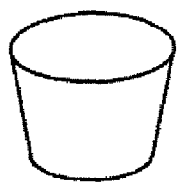
FIG. 7 A-J provide lateral and end-on views of various exemplary dental tips for an self-contained dental prophylaxis angle with an offset rotational axis according to the present invention.
Figure 7B:
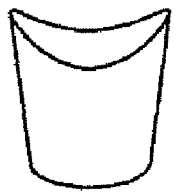
Figure 7C:
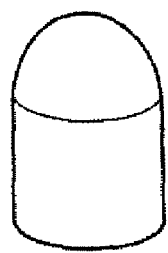
Figure 7D:
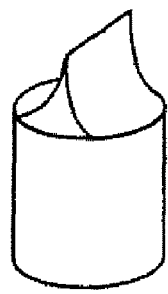
Figure 7E:
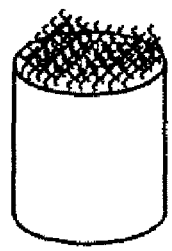
Figure 7F:
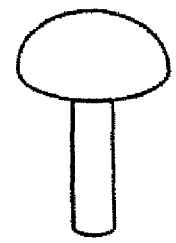
Figure 7G:
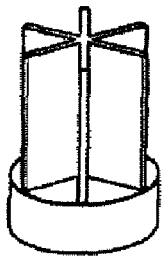
Figure 7H:
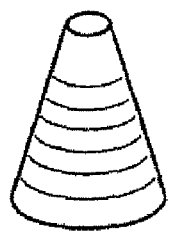
Figure 7I:
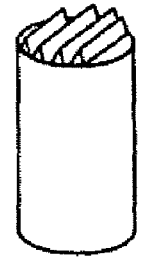
Figure 7J:

Yet another alternate embodiment according to the present invention is shown in FIG. 6. As shown in FIG. 6, an exemplary self-contained dental prophylaxis angle 600 is provided with a tubular body 605 with a proximal end 610 and a distal end 615. In various embodiments according to the present invention, the external shape of the body 605 may be round, oblong, triangular, square, polygonal, or any other desired shape. In the example illustrated in FIG. 6, the body 605 contains at least two parallel lumens, a content containing main lumen 618, and a separate drive lumen 625. The longitudinal axis of the main lumen 618 is referred to herein as the central axis. The drive lumen contains a drive shaft 630. The longitudinal axis of the drive shaft 630 is referred to herein as the rotational axis. At the proximal end 610, the drive shaft 630 extends along at least the proximal end 610 of the body 605 and is fitted with a geared connector 631 which interfaces with a transitional gear 632 compatible to connect operably with a standard concentric drive dental handpiece [not shown] to provide rotational power to said drive shaft 630. The drive shaft 630 is further provided with a distal gear tip 635 which interfaces with a geared tip 650 at a distal drive portal 638 to transfer rotational motion from the handpiece to the geared tip 650 thus rotating a cleaning tip 655 which is attached to said geared tip 650.

In alternate embodiments according to the present invention, the cleaning tip 655 and attached geared tip 650 are rotatably attached to the distal end 615 of the body 605, which may be straight, or may be curved at an angle varying from 0 to 179 degrees with respect to the long axis of the body 605. At or near the junction with the dental tip 655 and attached geared tip 650, the body 605 terminates with a content portal 660 which contains one or more fenestrations 665 to allow egress of therapeutic content 670 from main lumen 618 onto or in proximity with the dental tip 655 for cleaning or other therapeutic purposes. Flow of said egress of contained dentifrice or other therapeutic content 670 from main lumen 618 is effected by compression by a plunger 675 with a distal face 676. In various embodiments according to the present invention, the plunger 675 is sized and shaped to fit sealably, but slidably within the main lumen 618. The distal face 676 of the plunger 675 may be flat, concave, convex, or otherwise shaped to fit the desired application. The therapeutic content 670 is shown contained within a content sac 673 in the content containing main lumen 618.

In the example shown in FIG. 6, the plunger 675 is advanced by rotational action on a threaded control stem 696 which disengages engagement pin 682 from anchoring to dispensing notches 684 on the tubular body 605 to permit manual advancing pressure upon plunger 675 against the therapeutic content 670 to exit the content portal 660. The control stem 696 advances toward the distal end 615 of the content containing main lumen 618 along an advancement slot 686, assisted by manual pressure against the plunger 676. The engagement pin 682 is immediately renegagable with successive dispensing notches 684 upon opposite turning of the threaded control stem 696 which engages engagement pin 682 with anchoring to dispensing notches 684. The control stem 696 is alternatively spring loaded rather than threaded to effect disengagement and re-engagement of the engagement pin 682 with the dispensing notches 684.

Prophylaxis angles according to the present invention as shown in FIGS. 1-6 may be provided either as single use, disposable units or for multiple use applications. Such prophylaxis angles may be fabricated out of any biocompatible material, including but not limited to, plastics, high durometer rubbers, other polymers, aluminum, stainless steel, other metals, metal alloys, or combinations thereof Exemplary embodiments of various dental tips for a prophylaxis angle according to the present invention are shown in FIGS. 7(A)-7(J). Such dental tips may be fabricated of plastic, natural or synthetic rubbers, other polymers, nylon, Teflon, plastic foam, metals, metal alloys, ceramics, natural bristles, or other synthetic or natural materials. Such dental tips may further be solid or of varying porosity. In addition, dental tips for a prophylaxis angle according to the present invention may be permanently attached to the prophylaxis angle, or may be removable for use of replacement or alternate form dental tips, as desired by the operator.

Dental tips for a prophylaxis angle according to the present invention may be provided with varying durometer material strength, yielding rigid, semi-rigid, or soft dental tips for various applications anticipated by the present invention. Similarly, the cross-sectional shape of various dental tips for a prophylaxis angle according to the present invention may vary for different applications. As shown in FIGS. 7(A)-7(J), such dental tips may be square, round, triangular, stellate, heart-shaped, polygonal, or irregular in their various cross-sectional shapes. Such dental tips may also be uniform in their long axis dimensions or may be tapered, irregular, or otherwise shaped for optimal use in a given dental therapeutic application.

The dentifrice or therapeutic content contained within a prophylaxis angle according to the present invention may be a cleaning paste, a bleaching or etching agent, an antibacterial agent, topical fluoride or calcium treatment, desensitizing treatment, or any other desired therapeutic material or any combination thereof that may be prepared, contained, and delivered in a paste, gel, or other semisolid form. A dentifrice or therapeutic content according to the present invention may also include a surfactant or other chemical, biological, or mechanical agent to aid in the performance of a variety of dental therapeutic procedures.

Location of the drive mechanism needed to power motion of the dental tip in a position that is offset from the longitudinal axis of the body is important to the proper function of a dental prophylaxis angle according to the present invention. This offset location permits a mechanical and operational separation in the functions of providing power to the rotating dental tip and of dispensing dentifrice or other therapeutic content.

Many additional mechanisms are anticipated by the present invention to provide a controllable dispensing system for dentifrice or therapeutic content contained within an inventive prophylaxis angle. These include, but are not limited to, the use of spring-loaded components, such as a small controllably releasable spring-loaded motor, to controllably apply pressure within or to the portion of the prophylaxis angle containing such materials to effect such dispensing, the use of a telescoping rod or tubing within the body of such a prophylaxis angle to mechanically express such content, or use of a screw-mounted movable disk to serve as a plunger to effect such expression of content.

In yet another alternate embodiment according to the present invention, a prophylaxis angle may be provided with an offset drive mechanism and a dispensing system for contained dentifrice or other therapeutic medicaments in the form of a motorized toothbrush or other personal dental therapeutic device, designed for use by an operator and/or self use by a patient. In such an application, the prophylaxis angle has either a removable connection from a separate motorized handpiece to provide power, or such a motorized handpiece may be integrated into the prophylaxis angle to provide power and an operating handle.

Finally, while there have been shown and described and pointed out fundamental novel features of the present invention as applied to preferred embodiments thereof, it will be understood that various omissions and substitutions and changes in the form and details of the devices illustrated, and in their operation, and in the method illustrated and described, may be made by those skilled in the art without departing from the spirit of the invention as broadly disclosed herein. All of the above-discussed patents and publications are hereby expressly incorporated by reference as if they were written directly herein.

I claim:

1. A dental prophylaxis angle comprising:
    an elongated tubular body having a length defining a central axis and comprising a proximal end, a distal end, a main content lumen within the body in communication with a distal content portal, and a drive lumen within the body in communication with a distal drive portal, wherein the drive lumen is outside the content lumen, and wherein the proximal end elongated tubular body is connectable to a concentric drive dental handpiece;
    a dental tip rotatably mounted on the distal end;
    a mechanical drive shaft within the drive lumen and having a length defining a longitudinal rotational axis and having one or more distal gears extending through the drive portal in mechanical communication with the dental tip capable of imparting applied rotational motion to rotate the dental tip, wherein the longitudinal rotational axis of the drive shaft is mechanically offset from the central axis of the elongated tubular body along at least the proximal end of the tubular body;
    a geared connector operably coupled to the proximal end of the mechanically offset drive shaft, wherein the geared connector is operably connectable with the concentric drive dental handpiece;
    a content dispensing mechanism for selectively dispensing content through the content lumen and distal content portal into contact with the dental tip; and
    the content dispensing mechanism comprising a movable sealed plunger assembly within the content lumen,
    the plunger assembly located between the proximal end and the distal end of the tubular body,
    the content is enclosed between the plunger assembly and the distal end,
    whereby motion of the plunger assembly towards the distal end compresses the content and causes the content to be dispensed through the distal content portal.

2. A method of performing a dental therapeutic procedure on teeth, comprising using a dental prophylaxis angle of claim 1 with a content to effect a desired therapeutic treatment on teeth.

* * * * *